United States Patent
Cranenburgh et al.

(10) Patent No.: US 8,911,999 B2
(45) Date of Patent: Dec. 16, 2014

(54) SELF-DELETING PLASMID

(75) Inventors: Rocky Marc Cranenburgh, Keele (GB); Matthew William Leckenby, Peseux (CH)

(73) Assignee: Cobra Biologics Ltd., Keele (GB)

( * ) Notice: Subject to any disclaimer, the term of this patent is extended or adjusted under 35 U.S.C. 154(b) by 0 days.

(21) Appl. No.: 13/807,839

(22) PCT Filed: Jun. 28, 2011

(86) PCT No.: PCT/GB2011/000975
§ 371 (c)(1),
(2), (4) Date: Mar. 15, 2013

(87) PCT Pub. No.: WO2012/001352
PCT Pub. Date: Jan. 5, 2012

(65) Prior Publication Data
US 2013/0164790 A1 Jun. 27, 2013

(30) Foreign Application Priority Data
Jun. 30, 2010 (GB) .................................. 1011046.8

(51) Int. Cl.
*C12N 15/00* (2006.01)
*C12N 15/64* (2006.01)

(52) U.S. Cl.
CPC ..................................... *C12N 15/64* (2013.01)
USPC .......................................................... 435/455

(58) Field of Classification Search
None
See application file for complete search history.

(56) References Cited

PUBLICATIONS

Bloor et al., Applied and Environmental Microbiology, 2006, vol. 72, pp. 2520-2525.*
Lim et al., PNAS, 1987, vol. 84, pp. 6697-6701.*
Lederberg et al, Nature, 1946, vol. 158, p. 558.*
Kado et al., Journal of Bacteriology, 1981, vol. 145 pp. 1365-1373.*
International Search Report for PCT/GB2011/000975 mailed Oct. 21, 2011.
Written Opinion of the International Searching Authority mailed Oct. 21, 2011.
M. Leckenby et al., "Enhanced Vaccine Antigen Delivery by *Salmonella* Using Antibiotic-Free Operator-Repressor Titration-Based Plasmid Stabilisation Compared to Chromosomal Integration", Microbial Pathogenesis, vol. 46, No. 4, Apr. 1, 2009, pp. 201-206.
A. Cascioferro et al., "Xer Site-Specific Recombination, an Efficient Tool to Introduce Unmarked Deletions into Mycobacteria", Applied and Environmental Microbiology, vol. 76, No. 15, Jun. 11, 2010, pp. 5312-5316.
A. Bloor et al., "An Efficient Method of Selectable Marker Gene Excision by Xer Recombination for Gene Replacement in Bacterial Chromosomes", Applied and Environmental Microbiology, vol. 72, No. 4, Apr. 1, 2006, pp. 2520-2525.
H. Schweizer, "Bacterial Genetics: Past Achievements, Present State of the Field, and Future Challenges", Biotechniques, vol. 44, No. 5, Apr. 2008, pp. 633-641.
Colloms et al, "The ArcA/ArcB two-component regulatory system of *Escherichia coli* is essential for Xer site-specific recombination at *psi*", Molecular Microbiology (1998) 28(3), 521-530.
Reijns et al, "Mutagenesis of PepA suggests a new model for the *XerI cer* synaptic complex", Molecular Microbiology (2005) 57(4), 927-941.

* cited by examiner

*Primary Examiner* — Michele K Joike
*Assistant Examiner* — Mindy G Brown
(74) *Attorney, Agent, or Firm* — Nixon & Vanderhye P.C.

(57) ABSTRACT

A method of producing a selectable marker gene-free plasmid by culturing a plasmid containing a selectable marker gene flanked by site specific recombinase target sites in a host cell environment incapable of effecting recombination between the site specific recombinase target sites and subsequently culturing the plasmid in another host cell environment which is capable of effecting recombination between the site specific recombinase target sites, so that the selectable marker gene is excised. Uses of plasmids produced by the method for the production of recombinant protein for therapeutic and vaccine purposes, production of therapeutic DNA and DNA vaccines and delivery of recombinant protein and DNA to a patient using live bacterial vectors.

11 Claims, 5 Drawing Sheets

SELF-DELETING PLASMID

This application is the U.S. national phase of International Application No. PCT/GB2011/000975 filed 28 Jun. 2011 which designated the U.S. and claims priority to GB 1011046.8 filed 30 Jun. 2010, the entire contents of each of which are hereby incorporated by reference.

FIELD OF THE INVENTION

The present invention relates to methods of producing selectable marker gene-free plasmids. In particular the invention related to methods of culturing a plasmid containing a selectable marker gene under conditions which allow selection based on expression of the selectable marker gene, and the subsequent excision of the selectable marker gene. The invention also relates to uses of the plasmids produced by such a method for the production of recombinant protein for therapeutic and vaccine purposes, production of therapeutic DNA and DNA vaccines and delivery of recombinant protein and DNA to a patient using live bacterial vectors.

All documents referred to herein are incorporated by reference.

BACKGROUND OF THE INVENTION

Plasmids are self-replicating DNA molecules that exist naturally in bacteria, archaea and some unicellular eukaryotes, such as yeast. In recent years they have become essential to the biotechnology industry for the expression of recombinant protein genes and as DNA therapeutics and vaccines. For such applications plasmids encoding genes of interest are generally modified and replicated in a bacterial host cell such as *Escherichia coli*. Plasmids often encode an antibiotic resistance gene to enable antibiotic selection to be used to identify the cells which contain the plasmid following transformation, with the selective antibiotic added to the growth medium to kill cells that have lost the plasmid.

However, there are several disadvantages to using antibiotics for plasmid selection and maintenance. Firstly, the constitutive expression of the antibiotic resistance gene in the host cell produces a metabolic burden on the cell that reduces viability and increases the frequency of plasmid loss. Secondly, the antibiotics represent an additional contaminant in manufacture, and selection pressure is reduced by antibiotic degradation during fermentation. Thirdly, for DNA therapeutics and vaccines, the use of antibiotic resistance genes carries the risk of transfer to pathogens in the environment, leading to antibiotic resistant pathogenic strains. This is an acute risk when live bacterial strains are used as vectors for gene delivery to a patient. There is therefore a requirement to develop a mechanism of plasmid selection without the use of antibiotic resistance genes.

Alternative technologies have been developed that require an expressed selectable marker gene, such as a functional copy of an essential gene that complements a deleted copy on the host chromosome. The thymidylate synthase gene thyA (McNeil et al., 2000, Appl. Environ. Microbiol., 66: 1216-1219) or asd gene involved in diaminopimelic acid synthesis (Degryse 1991, Mol. Gen. Genet. 227: 49-51) have been used as the selective genes on plasmids in cells where the chromosomal genes are non-functional. Both this approach and antibiotic selection share the same important drawback: the presence and expression of a selectable marker gene that results in a significant metabolic burden to the cell and makes plasmid loss selectively advantageous (Bentley et al. 1990, Biotechnol. Bioeng. 35: 668-681).

Two further technologies have been developed which circumvent the requirement for selectable marker gene expression, and therefore lead to a reduced metabolic burden on the cell. ORT (Operator-Repressor Titration) utilises a modified bacterial cell where an essential chromosomal gene is placed under the control of an inducible promoter. A repressor protein binds to operator sequences adjacent to the promoter to prevent expression of the essential gene, thus causing the cell to die unless an inducer is present. When an ORT bacterial cell is transformed with a multi-copy plasmid containing the operator sequence, the repressor is titrated by the plasmid and the expression of the essential gene is enabled, thus allowing cell growth and therefore plasmid selection and maintenance (Cranenburgh et al. 2001. Nucleic Acids Res. 29: e26).

The other selectable marker gene-free system, oriSELECT, utilises the pMB1 origin of replication that is found on the majority of plasmids used in molecular genetics research and development. The pMB1 on naturally produces an anti-sense RNA to regulate its copy number, and oriSELECT cells are modified such that this RNA interacts with the mRNA of a corresponding sense sequence engineered in a gene fusion with either a repressor regulating an essential gene, or a toxin gene, such that the presence of the plasmid is required for cell survival (Cranenburgh 2005, WO06/003412).

The disadvantage of both of these selectable marker gene-free expression systems is that the chromosomes of the microbial cells need to be genetically modified. This can be technically challenging in many species, and even in species that are readily amenable to genetic manipulation it is time-consuming and laborious. There therefore remains a need to develop a plasmid selection system would be free from selectable marker genes and which would not require genetic modification of the host cell.

DESCRIPTION OF THE INVENTION

The inventors have developed a system of producing a selectable marker gene-free plasmid. In developing this system the inventors have surprisingly discovered that a selectable marker gene-free plasmid can be maintained in a host cell without a plasmid maintenance system. This finding is unexpected because the skilled person would have expected a plasmid to have been lost from a host cell in the absence of a plasmid maintenance system. This surprising finding is likely to be due to the large decrease in the metabolic burden placed in the cell following the excision of the selectable marker gene.

Therefore, in a first aspect the invention relates to a method of producing a selectable marker gene-free plasmid comprising the steps of:
a) culturing a plasmid containing a selectable marker gene flanked by site specific recombinase target sites in a first host cell environment which is incapable of effecting recombination between the site specific recombinase target sites; and
b) subsequently culturing the plasmid in a second host cell environment which is capable of effecting recombination between the site specific recombinase target sites, such that the selectable marker gene is excised.

Host Cell Environment

The term "host cell environment" encompasses the host cell itself and the conditions of the host cell environment. Therefore, the host cell environment is altered if the plasmid is moved from a first host cell to a second host cell or if the conditions of the host cell are altered. In the later case the first and second host cell environments are temporally separated. Conditions in a host cell are generally altered by altering the conditions in which the cell is cultured. The conditions which may be altered include but are not limited to osmolarity, temperature, the presence or absence of an inducer, the growth phase of the cell and the presence of chemicals that alter DNA secondary structure or supercoiling.

Therefore, in a second aspect the invention relates to a method of producing a selectable marker gene-free plasmid comprising the steps of:
a) culturing a plasmid containing a selectable marker gene flanked by site specific recombinase target sites in a first host cell which is incapable of effecting recombination between the site specific recombinase target sites; and
b) subsequently culturing the plasmid in a second host cell which is capable of effecting recombination between the site specific recombinase target sites, such that the selectable marker gene is excised.

In a third aspect the invention relates to a method of producing a selectable marker gene-free plasmid comprising the steps of:
a) culturing a plasmid containing a selectable marker gene flanked by site specific recombinase target sites in a host cell at an osmolarity which makes it incapable of effecting recombination between the site specific recombinase target sites; and
b) subsequently altering the osmolarity of the host cell so that it is capable of effecting recombination between the site specific recombinase target sites, such that the selectable marker gene is excised.

In a fourth aspect the invention relates to a method of producing a selectable marker gene-free plasmid comprising the steps of:
a) culturing a plasmid containing a selectable marker gene flanked by site specific recombinase target sites in a host cell at a temperature which makes it incapable of effecting recombination between the site specific recombinase target sites; and
b) subsequently altering the temperature of the host cell so that it is capable of effecting recombination between the site specific recombinase target sites, such that the selectable marker gene is excised.

In a fifth aspect the invention relates to a method of producing a selectable marker gene-free plasmid comprising the steps of:
a) culturing a plasmid containing a selectable marker gene flanked by site specific recombinase target sites in a host cell in the absence of an inducer so that it is incapable of effecting recombination between the site specific recombinase target sites; and
b) subsequently adding an inducer to the host cell so that it is capable of effecting recombination between the site specific recombinase target sites, such that the selectable marker gene is excised.

In a sixth aspect the invention relates to a method of producing a selectable marker gene-free plasmid comprising the steps of:
a) culturing a plasmid containing a selectable marker gene flanked by site specific recombinase target sites in a host cell in the presence of chemicals which alter the DNA secondary structure or supercoiling of the plasmid to render the cell incapable of effecting recombination between the site specific recombinase target sites; and
b) subsequently altering level of chemicals in the cell so that it is capable of effecting recombination between the site specific recombinase target sites, such that the selectable marker gene is excised.

In a seventh aspect the invention relates to a method of producing a selectable marker gene-free plasmid comprising the steps of:
a) culturing a plasmid containing a selectable marker gene flanked by site specific recombinase target sites in a first host cell in the absence of a site specific recombinase capable of acting upon the site specific recombinase target sites so that the cell is incapable of effecting recombination between the site specific recombinase target sites; and
b) subsequently culturing the plasmid in a second host cell in the presence of a site specific recombinase capable of acting upon the site specific recombinase target sites, such that the selectable marker gene is excised.

In one embodiment the host cell environment may be altered by one or more of the changes described above.

Site Specific Recombinase

In one embodiment, the method of the invention utilises endogenous site specific recombinases to effect selectable marker gene excision in the second host cell environment. This is advantageous because it removes the need to genetically modify the host cell, making the method both simpler and more efficient. The term "endogenous" is used to mean that the site specific recombinases originate from the same cell type as the second host cell environment. Generally the site specific recombinases will originate from the second host cell environment i.e. the second host cell environment will not have been genetically manipulated in order to contain genes capable of expressing the site specific recombinases.

It will be apparent to the skilled person that the nature of the endogenous site specific recombinase which acts upon the plasmid in the method of the invention will depend upon the nature of the site specific recombinase target sites which are present within the plasmid.

The utilisation of endogenous site specific recombinases is advantageous over the prior art because it does not require the introduction of an exogenous recombinase in trans. This simplifies the method, making it quicker, cheaper and more efficient because modification of the host cell environment to express the recombinase is not required. In a further embodiment the endogenous site specific recombinases may include one or more of XerC, XerD, CodV, RipX, Cre, Int, X is, P22, Flp and R1.

In one embodiment the endogenous site specific recombinase may be selected from Cre, Flp, R, XerC, XerD, RipX and CodV.

In another embodiment the endogenous site specific recombinases may be transposases.

Preferably the site specific recombinases are XerC and XerD. More preferably the XerC and XerD site specific recombinases are endogenous.

The Xer recombination system in prokaryotes is essential to ensure correct chromosomal segregation following replication, and to restore the chromosome dimers generated by RecA back to monomers, allowing replicated chromosomes to segregate. Xer recombinases are members of the tyrosine recombinase family and are represented by XerC and XerD in Gram-negative bacteria such as *Escherichia coli* (Blakely et al. Cell 1993, 75: 351-361), and by CodV and RipX in *Bacillus subtilis* and other Gram-positive bacteria (Sciochetti et al. 1999, J. Bacteriol. 181: 6053-6062). Xer recombinases act on chromosomes at the 28 base pair target sequence known as dif (Leslie and Sherratt 1995, EMBO J. 14: 1561-1570; Sciochetti et al. 2001, J. Bacteriol. 183: 1058-1068). The protein FtsK is necessary for Xer recombination in *E. coli* (Recchia et al. 1999, EMBO J. 18: 5724-5734), and FtsK homologues are widely conserved in bacteria, but are not found in archaea (Recchia and Sherratt 1999, Mol. Microbiol. 34: 1146-1148).

The endogenous Xer recombination system has previously been used in a technique ('Xer-cise') to excise antibiotic resistance genes from chromosomes following integration of a linear DNA molecules in host cell chromosomes (Bloor and Cranenburgh 2006, Appl. Environ. Microbiol. 72: 2520-2525).

The endogenous Xer recombination system also functions to resolve plasmid dimers. In order to facilitate recombination plasmid dimers contain site specific recombinase recognitions sites which are functionally equivalent to dif. These sites are cer and psi. cer is found in the *E. coli* plasmid ColE1 (Summers and Sherratt 1984, Cell 36: 1097-1103), and psi is found in the *Salmonella* plasmid pSC101 (Cornet et al. 1994, J. Bacteriol. 176: 3188-3195).

When a plasmid dimer is formed, the Xer recombination system acts to convert the dimer back to two monomers by carrying out DNA recombination at the cer and psi sites. However, unlike the chromosomal dif site, XerC and XerD only act on plasmid target sites if accessory sequences of ~180 bp are also present (Hayes and Sherratt, 1997). These accessory sequences for cer are the binding sites for the proteins PepA (aminopeptidase A) and ArgR (argenine biosynthesis pathway repressor), and for psi are binding sites for the proteins PepA and ArcA (Colloms et al. 1998, Mol Microbiol. 28: 521-530). This arrangement is required to ensure that Xer recombination is directional on plasmids i.e. only functions on directly repeating dimer resolution sites that are naturally formed by dimerisation.

The previously described Xer-cise system cannot be directly applied to plasmids because of the requirement for the accessory sequences in order to resolve plasmid dimers.

In one embodiment, the site specific recombinase may be inducible or constitutively expressed. In some embodiments, the site specific recombinase is preferably inducible. In particular, where the method of the invention utilises a first host cell environment and a second host cell environment that are present within the same host cell, the site specific recombinase is preferably inducible. Within this embodiment, expression of the recombinase may be induced by altering one or more of the osmolarity, the temperature, the presence or absence of an inducer, the growth phase of the cell and the presence of chemicals that alter DNA secondary structure or supercoiling.

Introduction of Recombinase

The preferred embodiment of the invention as described above does not require genetic modification of the second host cell environment, in which the plasmid is maintained. However, where site specific recombinases, such as the Xer recombinase system, are not naturally present in the second host cell environment the method of the invention may be carried out by introducing genes encoding suitable site specific recombinases or transposases into the host cell environment. This approach may also be used where site specific recombinases are present in the second host cell environment, but alternative site specific recombinases, which are naturally absent from the second host cell environment, are desired. In this embodiment genes encoding the alternative site specific recombinases may be introduced into the second host cell environment.

Genes encoding site specific recombinases may be introduced either on an extrachromosomal element or integrated into the host cell chromosome. Examples of recombinases suitable for introduction into the host cell environment include, but are not limited to Cre from bacteriophage P1 (Dale and Ow 1991, Proc. Natl. Acad. Sci. USA 88: 10558-10562), Int and X is from bacteriophages lambda (Zubko et al. 2000, Nature Biotechnol. 18: 442-445) and P22 (Wulff et al. 1993, Mol. Microbiol. 9: 261-271), Flp (Datsenko and Wanner 2000, Proc. Natl. Acad. Sci. USA 97: 6640-6645) and R (Sugita et al. 2000, Plant J. 22:461-469) from yeast. A transposase expressed in trans can also be used to excise a selectable marker gene flanked with internal resolution sites (Sanchis et al. 1997, Appl. Environ. Microbiol. 63: 779-784), and can therefore be introduced into the host cell environment in the same manner as a recombinase.

The selectable marker gene on the plasmid will be flanked by the site specific recombinase target site of the recombinase system which is introduced into the host cell environment. The method of the invention will function as described when using an endogenous site specific recombinase system.

Site Specific Recombinase Target Sites

The selectable marker gene present within the plasmid used in the method of the present invention is flanked by site specific recombinase target site.

A site specific recombinase target site is a portion of the DNA sequence of a chromosome or a plasmid to which a site specific recombinase is directed. When site specific recombinase target sites are present in tandem the sites are capable of being acted upon by one or more site specific recombinases to excise the portion of DNA located between the sites.

Within the scope of the present invention, the term site specific recombinase target site also includes transposase target sites.

As discussed above, the Xer recombinase system is endogenous to prokaryotes and utilises the tyrosine recombinases XerC and XerD to resolve both chromosome and plasmid dimers.

In one embodiment the site specific recombinase target sites may be capable of binding XerC and/or XerD.

In one embodiment the site specific recombinase target sites may be any XerC and/or XerD binding sites. Exemplary sites may be identified from host cell chromosomes and plasmids.

The site specific recombinase target sites may be formed by combining naturally-occurring plasmid dimer resolution sites from plasmids and chromosomes. An example of such a hybrid site is the dif-psi hybrid site also known as the pif site (Cornet et al. 1994, J. Bacteriol. 176: 3188-3195), the sequence of which is given in Table 1 below. The pif site differs in only one nucleotide from psi, but is capable of promoting Xer recombination on plasmids and chromosomes. Further hybrid sites for use in the process of the invention may be developed by generating hybrid sequences and determining the ability of these hybrid sequences to act as plasmid dimer resolution sites using simple recombination tests such as those described by Barre et al. 2000 (Genes Dev. 14: 2976-2988).

The local supercoiling of a chromosome or a plasmid is thought to be an important factor in Xer recombination, so there may be situations where the osmotic conditions or the surrounding DNA sequence can facilitate Xer recombination on plasmids via sites that normally function only on chromosomes, such as dif. Therefore, in one embodiment the site specific recombinase target site may be a dif site.

In a further embodiment, the site specific recombination sites may resemble any one of the sites listed in Table 1 below (i.e. SEQ ID NOs: 1-9) or any one of SEQ ID NOs: 17, 20 or 23. A site specific recombinase target site is considered to resemble one of SEQ ID NOs: 1-9, 17, 20 or 23 if it comprises or consists of any one of SEQ ID NOs: 1-9, 17, 20 or 23. A site specific recombinase target site is considered to resemble one of SEQ ID NOs: 1-9, 17, 20 or 23 if it has 50% or greater sequence identity to any one of SEQ ID NOs: 1-9, 17, 20 or 23. Alternatively, the site specific recombinase target site may have 60%, 70%, 80%, 85%, 90%, 95%, 99% or 100% sequence identity to one of SEQ ID NOs: 1-9, 17, 20 or 23. This may equate to a sequence having 1, 2, 3, 4 5, 6, 7, 8, 9, 10, 11, 12, 13, 14 or 15 nucleotide substitutions compared to any one of SEQ ID NOs: 1-9, 17, 20 or 23. Sequences comprising a fragment of 15, 16, 17, 18, 19, 20, 21, 22, 23, 24, 25, 26, 27, 28, 29, 30, 31, 32, 33 or 34 nucleotides of any one of SEQ ID NOs: 1-9, 17, 20 or 23 are also included within the scope of the invention. The fragment or variant sequences described above may be capable of binding XerC and/or XerD.

It will be apparent to the skilled person that the nature of the site specific recombinase target sites included in the plasmid will depend upon the site specific recombinases that are endogenous to first and second host cell environments in which the method of the invention is taking place.

The method of the invention provides an advantage over prior art processes in that it does not require the introduction of an exogenous recombinase in trans. The site specific recombinase target sites must therefore be capable of being acted on by endogenous site specific recombinases in the second cell environment. However, this does not mean that the site specific recombinase target sites must also be endogenous to the cell in which the process is taking place. For example, there is evidence that site specific recombinases from one species are able to act at site specific recombinase target sites from other species (Neilson et al. 1999, Mol. Microbiol. 31: 915-926). In addition, site specific recombinases have been shown to resolve sites that are different (Cornet et al. 1994, J. Bacteriol. 176: 3188-3195), e.g. an *E. coli* dif site and a psi-dif hybrid (pif site).

Eukaryotic cells also contain natural site specific recombinases which act to excise DNA between two site specific recombinase target sites. For example, the Flp recombinase of the yeast two-micron plasmid acts to invert a region of the plasmid by DNA recombination between FRT sites. Therefore, in one embodiment, the site specific recombinase target site may be an FRT site.

In one embodiment the site specific recombinase target sequences may be the same as each other. In another embodiment the site specific recombinase target sequences may be different from each other.

As discussed above, accessory sequences are required to direct site specific recombination between site specific recombinase target sites present on a plasmid. Therefore, in one embodiment one or more of the site specific recombinase target sites may be functionally associated with the binding sites for one or more accessory proteins.

The binding sites for accessory proteins are generally referred to as accessory sites.

In one embodiment the accessory sequences may be binding sites for one or more of the accessory proteins PepA, ArgR or ArcA. In specific embodiments the accessory sequences may contain binding sites for PepA and either ArgR or ArcA.

In one embodiment the accessory sequences may resemble the sequences shown below where the ArgR/ArcA binding sites are underlined with a dotted line, and XerCD binding sites are underlined with a single unbroken line. PepA binds to the accessory sequences around ArgR/ArcA binding sites, but the precise location has not been defined.

An accessory site is considered to resemble one of the sites listed below if it comprises or consists of any one of SEQ ID NOs: 17, 20 or 23. An accessory site is considered to resemble one of the sites listed below if it has 50% or greater sequence identity to any one of SEQ ID NOs: 17, 20 or 23. Alternatively, the accessory site may have 60%, 70%, 80%, 85%, 90%, 95%, 99% or 100% sequence identity to any one of SEQ ID NOs: 17, 20 or 23. This may equate to a sequence having 1, 2, 3 or 4 nucleotide substitutions compared to any one of SEQ ID NOs: 17, 30 or 23. Sequences comprising a fragment of 8, 9, 10, 11, 12, 13, 14, 15, 16, 17 nucleotides of any one of SEQ ID NOs: 17, 20 or 23 are also included within the scope of the invention. The fragment or variant sequences described above may be capable of binding PepA, ArgR or ArcA.

TABLE 1

Exemplary binding sites for site specific recombinases for use in the invention and their binding sites

| Site | Sequence (5'-3') | Recombinases | Origin | SEQ ID NO |
|---|---|---|---|---|
| Ecdif | GGTGCGCATAATGTATATTATGTTAAAT | XerC, XerD | *E. coli* chromosome | SEQ ID NO: 1 |
| cer | GGTGCGTACAATTAAGGGATTATGGTAAAT | XerC, XerD | *E. coli* plasmid ColE1 | SEQ ID NO: 2 |
| psi | GTGCGCGCAAGATCCATTATGTTAAAC | XerC, XerD | *Salmonella* plasmid pSC101 | SEQ ID NO: 3 |
| pif | GGTGCGCGCAAGATCCATTATGTTAAAT | XerC, XerD | dif-psi hybrid | SEQ ID NO: 4 |
| mwr | GGTGCACGCAACAGATGTTATGGTAAAT | XerC, XerD | *K pneumoniae* plasmid pJHCMW1 | SEQ ID NO: 5 |
| Bsdif | ACTTCCTAGAATATATATTATGTAAACT | CodV, RipX | *B. subtilis* chromosome | SEQ ID NO: 6 |
| loxP | ATAACTTCGTATAATGTATGCTATACGAAGTTAT | Cre | Bacteriophage P1 | SEQ ID NO: 7 |
| FRT | GAAGTTCCTATTCTCTAGAAAGTATAGGAACTT | Flp | Yeast | SEQ ID NO: 8 |
| RS | TTGATGAAAGAATACGTTATTCTTTCATCAA | R | Yeast | SEQ ID NO: 9 |

```
psi site and accessory sequences from pSC101
                                                                    (SEQ ID NO: 15)
gcctcccgtggggaaaaaatcatggcaattctggaagaaatagcgctttcagccggcaaacctgaagccggatctgcgattct gataacaaactagcaacaccagaacagcccgtttgcgggcagcaaaacccgtacttttggacgttccggcggttttttgtggcg agtggtgttcgggcggtgcgcgcaagatccattatgttaaacgggcga cer site and accessory sequences from ColEI
                                                                    (SEQ ID NO: 18)
gtgaaaccatgaaaaatggcagcttcagtggattaagtgggggtaatgtggcctgtaccctctggttgcataggtattcatacggt taaaatttatcaggcgcgatcgcgcagttttaggg tggtttgttgccattttacctgtctgctgccgtgatcgcgctgaacgcgttt tagcggtgcgtacaattaagggattatggtaaatccactt mwr site and accessory sequences from pJHCMW1
                                                                    (SEQ ID NO: 21)
aagaagaacatcggaaacaggacttactccggctgaatggtgtgaaattctgcgctatgcacttgcgcgcatactcatgcatgc cgtaaaaacagagcctgcgcgtttctggcgggttttcgggtggtttgttgcctgttttaccggtttcccgtcagaaacgccctgag ggcctctcaggcggtgcacgcaacagatgttatggtaaatacaatg
```

Selectable Marker Genes

A selectable marker gene may be any gene which can be used to detect the presence of a nucleic acid molecule.

In general, antibiotic resistance genes are used in the art to identify cells containing a particular nucleic acid molecule. Therefore in one embodiment the selectable marker gene is an antibiotic resistance gene which allows identification of cells containing the plasmid by culture in a medium containing the antibiotic. Antibiotic resistance genes are known in the art and any of these genes may be used. Examples of antibiotic resistance genes which may be used include, but are not limited to, genes which convey resistance to kanamycin, neomycin, streptomycin, gentamicin, ampicillin, chloramphenicol, tetracycline, neomycin, blasticidin, hygromycin, puromycin, erythromycin, lincomycin and zeocin. Other antibiotic resistance genes that may be used according to the invention are described in Neu 1992, Science 257 1064-1073.

In an alternative embodiment the selectable marker gene enables the production of a metabolite essential for but absent from the host cell environment. In one embodiment the selectable marker gene may be involved in the amino acid biosynthetic pathway of an amino acid which is not found in the media in which the cell is host cultured. In another embodiment the selectable marker gene may be the thymidylate synthase gene thyA or the asd gene involved in diampinopimelic acid synthesis.

A selectable marker gene-free plasmid is a plasmid which lacks a selectable marker gene.

First Host Cell Environment

The first host cell environment is incapable of effecting recombination between the site specific recombinase target sites which flank the selectable marker gene. Therefore the selectable marker gene will remain within the plasmid, allowing cells containing the plasmid to be selected on the basis of expression of the selectable marker gene.

In one embodiment, the cell is incapable of effecting recombination between the site specific recombinase target sites if less than 50% of plasmids undergo site specific recombination. In other embodiments the cell is incapable of effecting recombination between the site specific recombinase target sites if less than 40%, 30%, 20%, 15%, 10%, 5%, 3%, 2%, 1%, 0.5%, 0.1% or 0% of plasmids undergo site specific recombination.

Mutations

In one embodiment the first host cell environment may contain a mutation in a gene encoding one or more of the proteins involved in site specific recombination of a plasmid.

It is preferred that there is no mutation to the genes encoding the site specific recombinases such as XerC or XerD. This is because these proteins are required for chromosome segregation, and in the absence of functional versions of these proteins chromosome segregation will not occur and the first host cell environment will not be viable.

In one embodiment the chromosomal gene encoding one or more of the accessory proteins PepA, ArgR or ArcA may be mutated.

As discussed above, PepA and ArgR are required for site specific recombination of a plasmid at a cer site, whilst PepA and ArcA are required for site specific recombination at a psi site. A mutation in one or more of the genes encoding these accessory proteins will therefore prevent site specific recombination from occurring in the first host cell environment. Accordingly the selectable marker gene will be retained by the plasmid when present in the first host cell environment, and the selection pressure will be able to be used to select cells containing the plasmid.

The mutation to the genes encoding one or more the PepA, ArgR or ArcA proteins may be an inactivating mutation. Such a mutation may occur by means of addition, deletion or substitution of one or more of the nucleotides encoding one or more of these accessory proteins.

In another embodiment a mutation may be present in the first host cell environment which prevents one or more of the accessory proteins from being expressed. Such a mutation may be in a gene encoding a protein implicated in accessory protein expression. Alternatively, a repressor or antisense sequence which prevents translation of the accessory protein mRNA could be overexpressed.

In a preferred embodiment the first host cell environment contains a mutation in the PepA gene since this will render the cell incapable of recombination at either cer or psi sites.

The accessory protein mutant which is used as the first host cell environment may be a mutant *E. coli* strain selected from DS957, DS941 pepA, DS941 arcA2, DS941 arcA::Tn5(2.3) (Colloms et al. 1998 Mol. Microbiol. 28(3): 521-530), ECK4253 and ECK3226 (Baba et al. 2006, Mol. Systems. Biology (2006) doi:10.1038/msb4100050).

Osmolarity

In another embodiment the first host cell environment may be incapable of effecting recombination between the site specific recombination sites because the osmolarity of the first host cell environment will not allow recombination to occur.

Within the embodiment the site specific recombinase target site may be the mwr site from the *Klebsiella pneumoniae* plasmid pJHCMW1. This site is related to cer and is adjacent to accessory sequences that bind PepA and ArgR (Pham et al. 2002, J. Bacteriol. 184: 1607-1616). This osmoregulatged sequence does not enable efficient Xer recombination under high salt concentrations, but Xer recombination is enabled when the salt concentration is below 0.5% NaCl in L broth, due to resulting changes in DNA supercoiling (Trigueros et al. 2009, Nucleic Acids Res. 37: 3580-3587).

Therefore, in this embodiment the first host cell environment may have an osmolality of greater than or equal to 209 mmol/kg (0.5% NaCl). The osmolarity of the first host cell environment may be maintained at a level above that required for complete recombination of all plasmids in the population by culturing the first host cell environment in a medium containing 0.5%, 0.4%, 0.3%, 0.2%, or 0.1% NaCl, as this concentration range enables a sufficient proportion of un-recombined plasmids to persist. Ideally, the concentration of the first host cell environment is greater than 0.5%. The second environment to which the host cell is transferred will have less than 0.1% NaCl, and ideally 0% NaCl.

Temperature

In another embodiment the first host cell environment may be incapable of effecting recombination between the site specific recombination sites because the temperature of the first host cell environment is either above or below that required to effect recombination.

Inducers

In another embodiment the first host cell environment may be incapable of effecting recombination between the site specific recombinase target sites because of the absence of an inducer in the first host cell environment. Such an inducer may be required for recombination to occur.

Chemicals which Alter the Secondary Structure or Supercoiling of the Plasmid

In order for recombination between site specific recombinase target sites to occur, the plasmid must have the correct secondary structure and supercoiling for the recombinases and accessory proteins to access the site specific recombinase target sites and accessory sequences, respectively. Therefore, in one embodiment the first host cell environment may be incapable of effecting recombination between the site specific recombinase target sites because of the presence of a chemical which produces a plasmid secondary structure or supercoiling which does not allow the site specific recombinases and/or accessory proteins access to the relevant sites on the plasmid. Such a chemical may intercalate DNA, such as ethidium bromide.

Absence of Site Specific Recombinase

In a further embodiment the first host cell environment may be incapable of effecting recombination between the site specific recombinase target sites due to the absence of a site specific recombinase able to act upon the site specific recombinase target sites.

Second Host Cell Environment

The second host cell environment is capable of effecting recombination between the site specific recombinase target sites which flank the selectable marker gene. Therefore the selectable marker gene will be excised from the plasmid by recombination between the site specific recombinase target sites flanking the selectable marker gene.

In one embodiment, the cell is capable of effecting recombination between the site specific recombinase target sites if more than 1% of cells are capable of performing site specific recombination on the plasmid. In other embodiments the cell is capable of effecting recombination between the site specific recombinase target sites if more than 2%, 3%, 4%, 5%, 10%, 20%, 30%, 40%, 50%, 60%, 70%, 80%, 85%, 90%, 95%, 97%, 98%, 99%, 99.5%, 99.9% or 100% of plasmids undergo site specific recombination.

Active PepA, ArgA and ArcA

In the embodiment where the first host cell environment contains an inactivating mutation in one or more of the genes encoding the accessory proteins PepA, ArgR and ArcA, the second host cell environment may contain active versions of one or more of PepA, ArgR and ArcA. Preferably the second host cell environment contains an active version of PepA and at least one of ArgR and ArcA so that recombination can be effected at cer or psi sites. In one embodiment the second host cell environment may contain an active version of whichever accessory protein is inactivated in the first host cell environment.

Osmolarity

In the embodiment where the first host cell environment is maintained at an osmolarity below that required for recombination to occur, the second host cell environment may be made capable of effecting recombination by displaying an osmolarity greater than that required to effect recombination.

This embodiment may occur when the site specific recombinase target site resembles the mwr site from the *Klebsiella pneumoniae* plasmid pJHCMW1.

In this embodiment the second host cell environment may have an osmolarity due to a concentration of less than 0.5% salt. In one embodiment the osmolarity in the first host cell environment may be due to a concentration of more than 0.55%, 0.6%, 0.7%, 0.8%, 0.9%, 1% or more salt.

It will be apparent to a person skilled in the art that the osmolarity may be altered between the first host cell environment and the second host cell environment in a variety of ways. In one embodiment the osmolarity may be altered by diluting the first host cell environment with medium free of salt in order to convert it to the second host cell environment. Alternatively, cells from the first medium containing salt are centrifuged to produce a cell pellet, the supernatant containing salt is removed, and the cells are resuspended in a medium that is free of salt.

Temperature

In the embodiment where the first host cell environment is maintained at a temperature either above or below that required to effect recombination, the second host cell environment may be made capable of effecting recombination by displaying a temperature greater than or less than that required to effect recombination.

It will be apparent to a person skilled in the art that the temperature may be altered between the first host cell environment and the second host cell environment in a variety of ways. In one embodiment the temperature may be altered by altering the temperature at which the host cell is cultured.

Inducers

In the embodiment where the first host cell environment is incapable of effecting recombination between the site specific recombinase target sites because of the absence of an inducer in the first host cell environment, the second host cell environment may be made capable of effecting recombination by the addition of an inducer.

It will be apparent to a person skilled in the art that an inducer may be added to a cell in a variety of ways. In one embodiment the inducer may be added by adding the inducer to the medium in which the host cell is being cultured in order to convert it from a first host cell environment to a second host cell environment.

Chemicals which Alter the Secondary Structure or Supercoiling of the Plasmid

In the embodiment where the first host cell environment is incapable of effecting recombination between the site specific recombinase target sites because of the presence of a chemical which produces a plasmid secondary structure or supercoiling which does not allow the site specific recombinases and/or accessory proteins access to the relevant sites on the plasmid, the second host cell environment may be made capable of effecting recombination by the removal of the chemical.

It will be apparent to a person skilled in the art that a chemical may be removed from a cell in a variety of ways. Cells from the first medium containing the chemical may be centrifuged to produce a cell pellet, the supernatant containing the chemical may be removed, and the cells resuspended in a medium that is free of the chemical.

Presence of Site Specific Recombinase

In the embodiment where the first host cell environment is incapable of effecting recombination between the site specific recombinase target sites due to the absence of a site specific recombinase able to act upon the site specific recombinase target sites, the second host cell environment may be capable of effecting recombination between the site specific recombinase target sites due to the presence of a site specific recombinase able to act upon the site specific recombinase target sites.

The site specific recombinase able to act upon the site specific recombinase target sites may be encoded upon a separate plasmid present within the second host cell environment or, where the second host cell environment is a separate host cell, the site specific recombinase may have been incorporated into the chromosome of the second host cell.

Selection of Host Cell Environment

In one embodiment the second host cell may be a member of the enterobacteriaceae (e.g. the genera *Escherichia, Shigella*, or *Salmonella*). Within this embodiment, the first host cell environment may be an *E. coli* strain containing a pepA or argR/arcA mutant. This ensures that the XerC and XerD proteins present within the first host cell environment are incapable of recombining the site specific recombinase target sites within the first host cell environment.

This embodiment may also arise if the Xer recombinases and accessory protein target sites required for recombination in the second host cell environment are present in the first host cell environment.

However, where the first host cell environment is sufficiently evolutionarily divergent from the second host cell environment such that its Xer recombination system does not function on the site-specific recombinase recognition site on the plasmid in the first host cell environment, then the first host cell environment does not need to be a pepA or argR/arcA mutant.

In another embodiment, the first host cell environment may be a prokaryotic cell, and the plasmid may contain FRT site specific recombinase target sites. Since prokaryotic cells do not contain the Flp recombinase required to recombine FRT sites, the site specific recombinase target sites will not be recombined in the first host cell environment, and no mutation to the genes encoding one or more of the accessory proteins is required in the first host cell environment. In this embodiment, the second host cell environment should be a eukaryotic cell capable of site specific recombination between FRT sites, such as a yeast cell, so that recombination between the FRT sites can occur in the second host cell environment to excise the selectable marker gene.

Host Cell Transformation

It will be understood that the first host cell environment will be transformed with a plasmid containing a selectable marker gene flanked by site specific recombinase target sites.

In embodiments where the first host cell environment and the second host cell environment are formed in different cells, the plasmid containing a selectable marker gene flanked by site specific recombinase target sites will be removed from the first host cell environment and transformed into the second host cell environment. Methods of host cell transformation are well known in the art and are described, for example in Sambrook (Molecular Cloning; A Laboratory Manual, Second Edition, 1989). Methods for isolating the plasmid containing a selectable marker gene flanked by site specific recombinase target sites from the first host cell environment are also well known in the art and are described for example in Sambrook (Molecular Cloning; A Laboratory Manual, Second Edition, 1989). In a preferred embodiment transformation may be conducted by electroporation.

In embodiments where the first host cell environment and the second host cell environment are formed in different cells the methods of transformation of the plasmid into each host cell environment may be the same or may be different.

Cell Culture

In the first step, the plasmid containing a selectable marker gene flanked by site specific recombinase target sites is cultured in a first host cell environment under conditions which make it incapable of effecting recombination between the site specific recombinase target sites. Within this step, the cell may be cultured in the presence of a selective pressure so that only cells which contain the plasmid are maintained.

In the second step the plasmid containing a selectable marker gene flanked by site specific recombinase target sites is cultured in a second host cell environment under conditions which make it capable of effecting recombination between the site specific recombinase target sites, such that the selectable marker gene is excised. Suitable conditions of cell culture are known in the art. In one embodiment the cell culture conditions may include a temperature of 25-42° C., ideally 30-37° C., in a broth culture or agar plate providing all the nutrients required for growth. The most common conditions would be at 37° C. on LB agar or in LB broth.

It will be apparent to a person skilled in the art that the selectable marker gene will not be excised instantaneously. Therefore, the second host cell environment may initially include the presence of a selective pressure to ensure that only cells which contain the plasmid are initially maintained.

In one embodiment the method may additionally include the step of maintaining the selectable marker gene-free plasmid in cell culture. This step may follow the excision of the selectable marker gene.

The inventors have surprisingly discovered that a selectable gene-free plasmid produced according to the method of the invention can be maintained in the second host cell environment in the absence of a plasmid maintenance system. This is surprising because the skilled person would have expected a plasmid to be lost in the absence of a plasmid maintenance system. It is likely that plasmids produced according to the method of the invention are maintained due to a decreased metabolic burden in the absence of the expression of a selectable marker gene.

In a further embodiment the method may additionally comprise the step of isolating the selectable marker gene-free plasmid from the first and/or second host cell environment. Methods of plasmid isolation are well known in the art and include, but are not limited to centrifugation and purification by alkaline lysis according to methods based on Birnboim and Doly 1979, Nucleic Acids Res. 7: 1513-1523. The DNA may be analysed following extraction from the second host cell environment.

Host Cell Types

The first and second host cell environments may be formed from any cell type. The first and second host cell environments may be the same cell type or they may be different cell types. Where the first and second host cell environments are the same cell type they may be different strains. In the embodiment where the first and second host cell environments are formed in the same cell the first and second host cell environments will be of the same cell type.

In one embodiment the first host cell environment and/or the second host cell environment may be a prokaryotic cell. Within this embodiment the first host cell environment and the second host cell environment may be a bacterial cell.

In one embodiment the first host cell environment and/or the second host cell environment may be a Gram-negative bacterial cell. Within this embodiment the first host cell environment and the second host cell environment may be independently selected from the genera *Escherichia, Salmonella, Shigella, Agrobacterium, Pseudomonas* and *Vibrio*. Further within this embodiment the first host cell environment and the second host cell environment may be independently selected from *Escherichia coli* and *Salmonella enterica* (including Serovars *Typhi* and *Typhimurium*).

In another embodiment the first host cell environment and/or the second host cell environment may be a Gram-positive bacterial cell. Within this embodiment the first host cell environment and the second host cell environment may be independently selected from the genera *Bacillus, Streptomyces, Listeria, Lactobacillus, Lactococcus* and *Mycobacterium*. Further within this embodiment the first host cell environment and the second host cell environment may be independently selected from *Bacillus subtilis* or *Mycobacterium bovis* (e.g. strain BCG).

In another embodiment the first host cell environment and/or the second host cell environment may be an archaeon. Within this embodiment the first host cell environment and/or the second host cell environment may be yeast. Further within this embodiment the first host cell environment and the second host cell environment may be independently selected from the genera *Hansenula, Pichia, Saccharomyces* and *Schizosaccharomyces*.

In another embodiment the first host cell environment and/or the second host cell environment may be a non-fungal eukaryote capable of replicating a plasmid. Within this embodiment the first host cell environment and the second host cell environment may be independently selected from the genera *Chlamydomomas, Dictyostelium* and *Entamoeba*.

Where the cell is a prokaryotic cell, it may be a RecA$^+$ cell or a RecA$^-$ cell.

Within the scope of the invention, any of the proposed host cell types may be attenuated or non-attenuated host cells.

It will be understood that all combinations of the first and second host cell environments are contemplated within the scope of the invention.

Gene of Interest

In one embodiment the plasmid used in the method of the invention contains a gene of interest. The gene of interest may encode any nucleic acid or protein which it is desired to produce recombinantly or which can be used therapeutically.

In a further embodiment the gene of interest may be a therapeutic or prophylactically useful protein. In another embodiment the gene may be a gene suitable for use as a vaccine.

One Step Method

Generally the method of the invention will be carried out as described above, using a first host cell environment and a second host cell environment. However, in an alternative embodiment the plasmid may be synthesised or ligated chemically and transformed directly into the second host cell environment. This method would negate the requirement for the first host cell environment. The invention therefore encompasses a method which utilises a single host cell environment which is capable of effecting recombination between the site specific recombinase target sites, such that the selectable marker gene is excised.

This alternative method maintains the surprising advantage that the plasmid is maintained within the second host cell environment following excision of the selectable marker gene, in the absence of a plasmid maintenance system.

Plasmid

In one embodiment the invention also encompasses the selectable marker gene-free plasmid produced by the method of the invention. This plasmid may be isolated and/or purified from the second host cell environment.

In another embodiment the invention also includes the second host cell environment containing a selectable marker gene-free plasmid produced by the method of the invention.

In another embodiment the invention includes a composition comprising a plasmid produced according to the method of the invention and a pharmaceutically acceptable excipient.

Host Cell Containing the Plasmid

In one embodiment the invention also encompasses a host cell containing a selectable marker gene-free plasmid. Such a host cell could also be said to be lacking a plasmid maintenance system. In one embodiment, the plasmid within the host cell contains a residual site specific recombinase target site. A residual site specific recombinase target site is one that is left on the plasmid following recombination between the two site specific recombinase target sites initially present. Therefore in one embodiment the plasmid within the host cell may contain a single site specific recombinase target site. This will allow a host cell containing a plasmid produced by the method of the invention to be distinguished from a host cell containing a plasmid produced by an alternative method, which would not contain a residual site specific recombinase target site. If required, the host cell may contain a plasmid maintenance system such as ORT (Operator Repressor Titration) or oriSELECT, as discussed above.

In one embodiment the host cell may contain a gene encoding an inducible site specific recombinase. The inducible site specific recombinase may be present on the host cell chromosome.

In one embodiment the host cell may be an unmodified host cell.

An unmodified host cell which does not contain a plasmid maintenance system can only be produced by a method according to the present invention because it was previously unexpected that a host cell which does not contain a plasmid maintenance system would retain a plasmid.

The host cell may be any cell type discussed above in relation to the method of the invention. For example, the host cell may be a Gram-negative bacterial cell (e.g. from the genera *Escherichia, Salmonella, Shigella, Agrobacterium, Pseudomonas* or *Vibrio*), a Gram-positive bacterial cell (e.g.

from the genera *Bacillus, Streptomyces, Listeria, Lactobacillus, Lactococcus* or *Mycobacterium*), an archaeon, a yeast cell (e.g. from the genera *Hansenula, Pichia, Saccharomyces* or *Schizosaccharomyces*), or a non-fungal eukaryote capable of replicating a plasmid (e.g. from the genera *Chlamydomonas, Dictyostelium* or *Entamoeba*).

The residual site specific recombinase target site contained on the plasmid in the host cell may be any site specific recombinase target site discussed in relation to the method of the invention including Ecdif, cer, psi, pif, mwr, Bsdif, loxP, FRT and RS.

Such a host cell may advantageously be use as a therapeutic or as a vaccine, as discussed below.

In another embodiment the invention includes a composition comprising an unmodified host cell containing a selectable marker gene-free plasmid and a pharmaceutically acceptable excipient.

Plasmid and Host Cell Uses

Within the scope of the invention, plasmids produced according to the method of the invention and host cells containing a plasmid in the absence of a plasmid maintenance system may have a number of uses.

Primarily, the plasmid produced according to the method of the invention and the host cells containing a plasmid in the absence of a plasmid maintenance system may be used in therapy. The therapy may be therapeutic or prophylactic.

Production of Recombinant Proteins as Therapeutics and Vaccines

In one embodiment the transformed cell containing the selectable marker gene-free plasmid (i.e. the second host cell environment) may be grown in a nutrient broth flask or fermenter to produce a recombinant protein that is later harvested for use as a protein therapeutic or a protein vaccine.

Production of Therapeutic DNA and DNA Vaccines

In another embodiment the transformed cell containing the selectable marker gene-free plasmid (i.e. the second host cell environment) may be grown in a nutrient broth flask or fermenter to produce a DNA sequence that is later harvested for use as a DNA therapeutic or DNA vaccine. The DNA therapeutic or DNA vaccine will generally take the form of a plasmid, but may also take the form of a linear DNA molecule through subsequent processing of the plasmid. Such processing may include the use of restriction endonucleases.

Delivery of Recombinant Protein and DNA to Animals Using Live Bacterial Vectors

In another embodiment, the transformed cell containing the selectable marker gene-free plasmid (i.e. the second host cell environment) can be administered directly to an animal in need of treatment. Within this embodiment the cell environment may be attenuated or non-attenuated. In this embodiment the cells may release their contents into the patient in order to produce a therapeutic or immunological effect. For example, attenuated *Salmonella* can be used to orally deliver a plasmid that expresses a recombinant antigen to the mucosal immune system in the lining of the gastrointestinal tract (Leckenby et al. 2009, Microb. Pathog. 46: 201-206). Alternatively, the second host cell environment containing the selectable marker gene-free plasmid, e.g. when the cell is a member of the genus *Agrobacterium*, may be used to deliver plasmid DNA directly to plants to enable genetic modification (Ebinuma et al. 2001, Plant Cell Rep. 20: 383-392).

The selectable marker gene-free plasmid or the cell containing the plasmid described above may be administered to a patient by any method known in the art. These methods include but are not limited to oral, intradermal, subcutaneous, intramuscular, intramucosal, intravenous, intraperitoneal or nasal administration.

Within the scope of the invention, the patient to be treated may be any animal in need of treatment. This includes humans, fish, dogs, cats, monkeys, goats, camels, pigs, sheep, rats, mice, and horses.

In another embodiment the invention includes a method of vaccinating or treating a patient comprising administering to the patient a transformed cell containing the selectable marker gene-free plasmid or a plasmid produced according to the method of the invention in a pharmaceutically acceptable amount.

In another embodiment the invention includes a transformed cell containing the selectable marker gene-free plasmid or a plasmid produced according to the method of the invention for use in vaccinating a patient or treating a disease in a patient.

In a further embodiment the invention includes a transformed cell containing the selectable marker gene-free plasmid or a plasmid produced according to the method of the invention for use in the manufacture of a medicament for vaccinating a patient or treating a disease in a patient.

Kits and Host Cells for Use in Kits

In one embodiment, the present invention encompasses a kit for performing the method of the invention.

The kit may comprise or consist of:
i) a first host cell environment containing a plasmid containing a selectable marker gene flanked by site specific recombinase target sites, wherein the first host cell environment is incapable of effecting recombination between the site specific recombinase target sites and;
ii) a second host cell environment which is capable of effecting recombination between the site specific recombinase target sites, such that the selectable marker gene is excised.

In one embodiment the first and second host cell environments in the kit may be present within separate cells, i.e. the kit comprises a first host cell and a second host cell. The host cells present within the kit may be of any cell type. In particular the host cells may be from any cell type discussed above in relation to the method of the invention.

The first host may contain a mutation in a gene encoding one or more of the proteins involved in site specific recombination of a plasmid. Preferably the chromosomal gene encoding one or more of the accessory proteins PepA, ArgR or ArcA may be mutated in the first host cell.

The second host cell may be capable of effecting recombination between the site specific recombinase target sites due to the presence of endogenous XerC/XerD and/or the an active version of one or more of the accessory proteins PepA, ArgR or ArcA.

The site specific recombinase target sites may be any site specific recombinase target sites discussed in relation to the method of the invention The kit may also comprise instructions.

The present invention also provides host cells suitable for use as this first host cell environment in the kits or methods of the invention. In particular, the present invention provides a host cell containing a plasmid containing a selectable marker gene flanked by site specific recombinase target sites, wherein the host cell further comprises an inactivating mutation in one of more of the chromosomal genes encoding one or more of the accessory proteins PepA, ArgR or ArcA.

The host cell according to this aspect of the invention may be from any cell type. In particular the host cell may be from any cell type discussed above in relation to the methods of the invention. The site specific recombinase target sites contained on the plasmid in the host cell described above and in the kit may be any site specific recombinase target sites discussed in relation to the methods of the invention. The selectable marker gene on the plasmid of these host cells may any selectable marker gene discussed above in relation to the methods of the invention.

The invention will now be described in more detail by way of examples. It will be appreciated that modifications may be made to the systems described in the Examples

EXAMPLE 1

Figure 1:
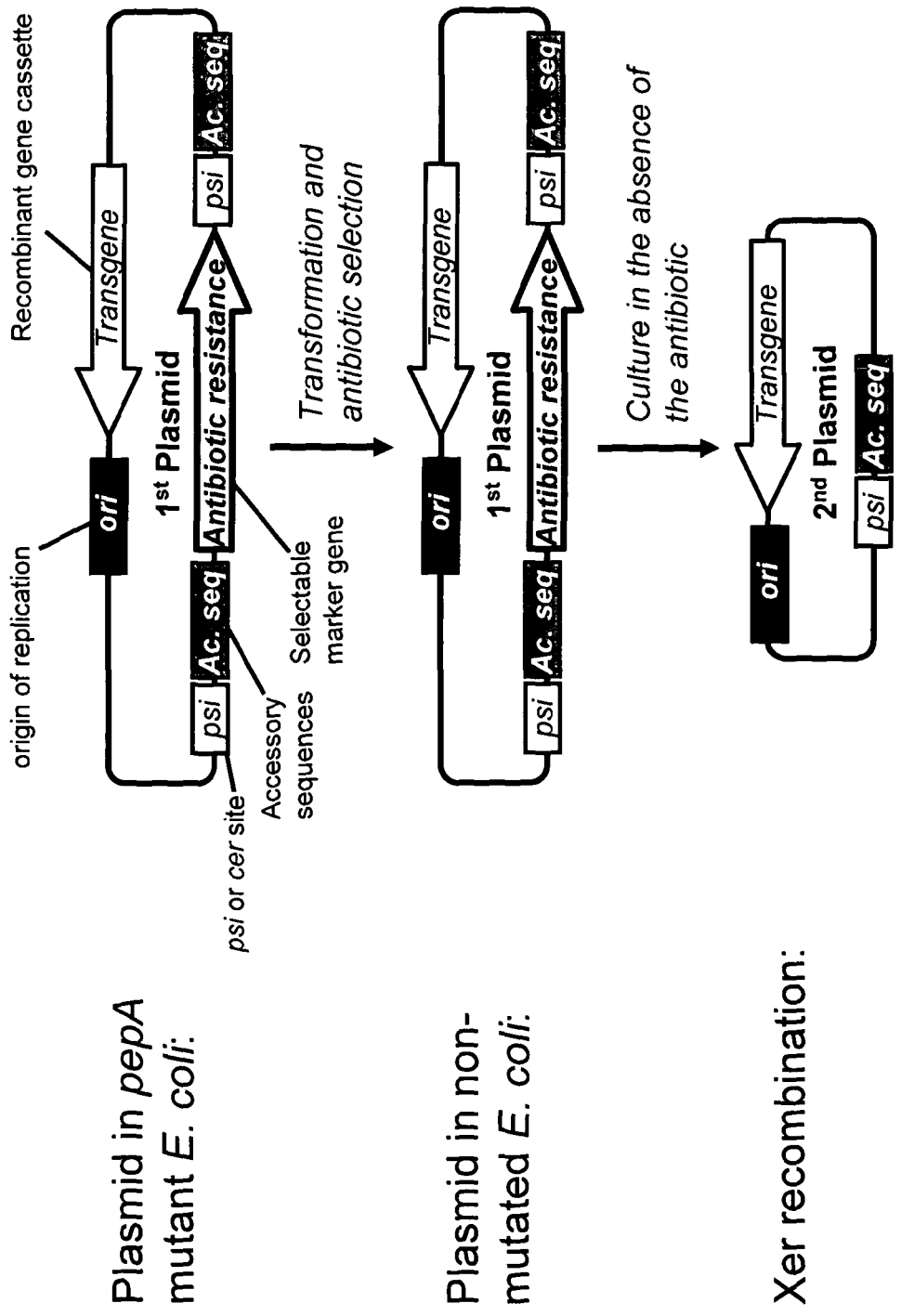
FIG. 1 shows an illustration of the processes by which an antibiotic resistance gene can be excised from a plasmid in a preferred embodiment of the invention.
Figure 2:
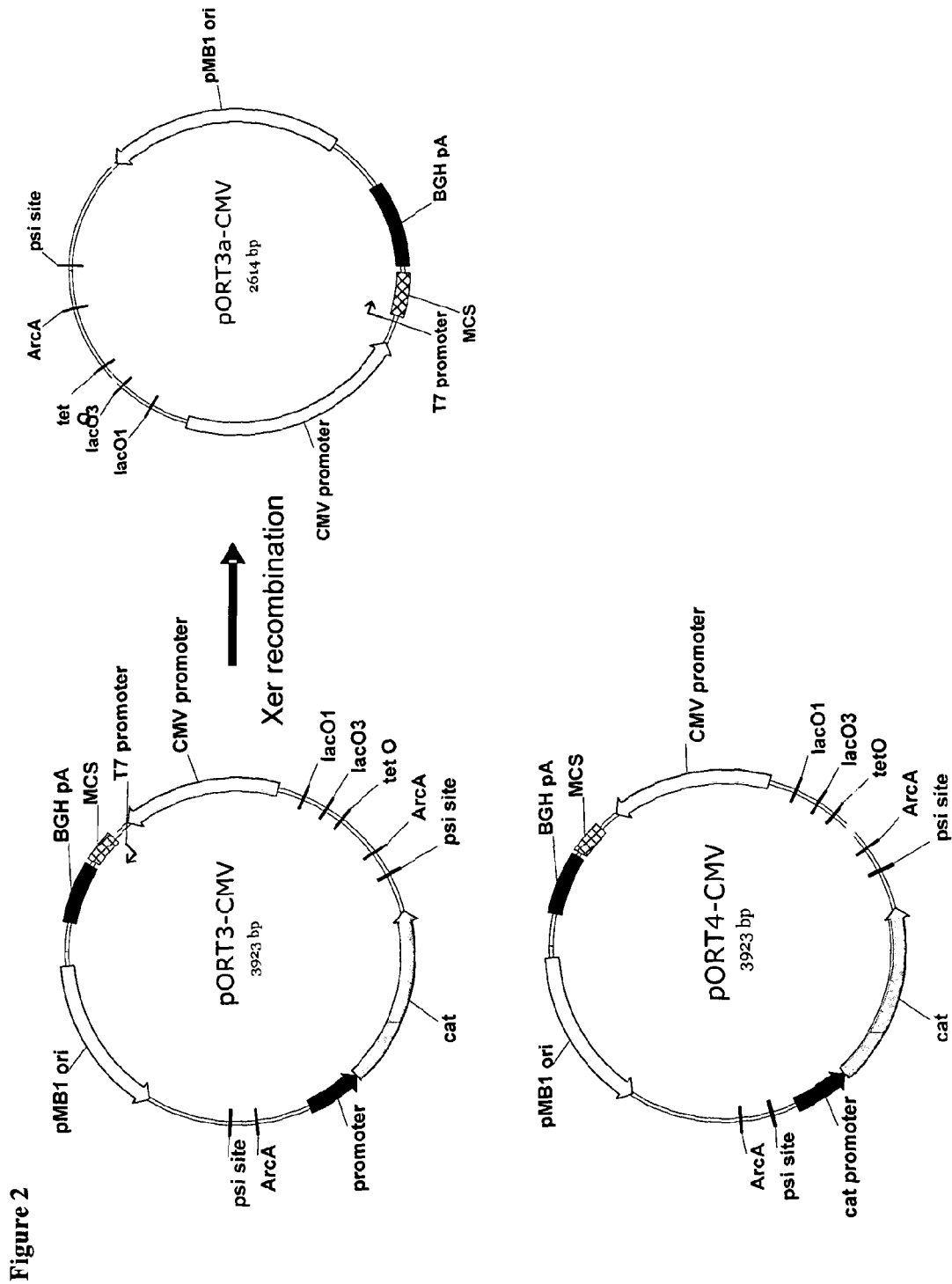
FIG. 2 shows a representation of the plasmids pORT3CMV, pORT3aCMV and pORT4CMV.
Figure 3:
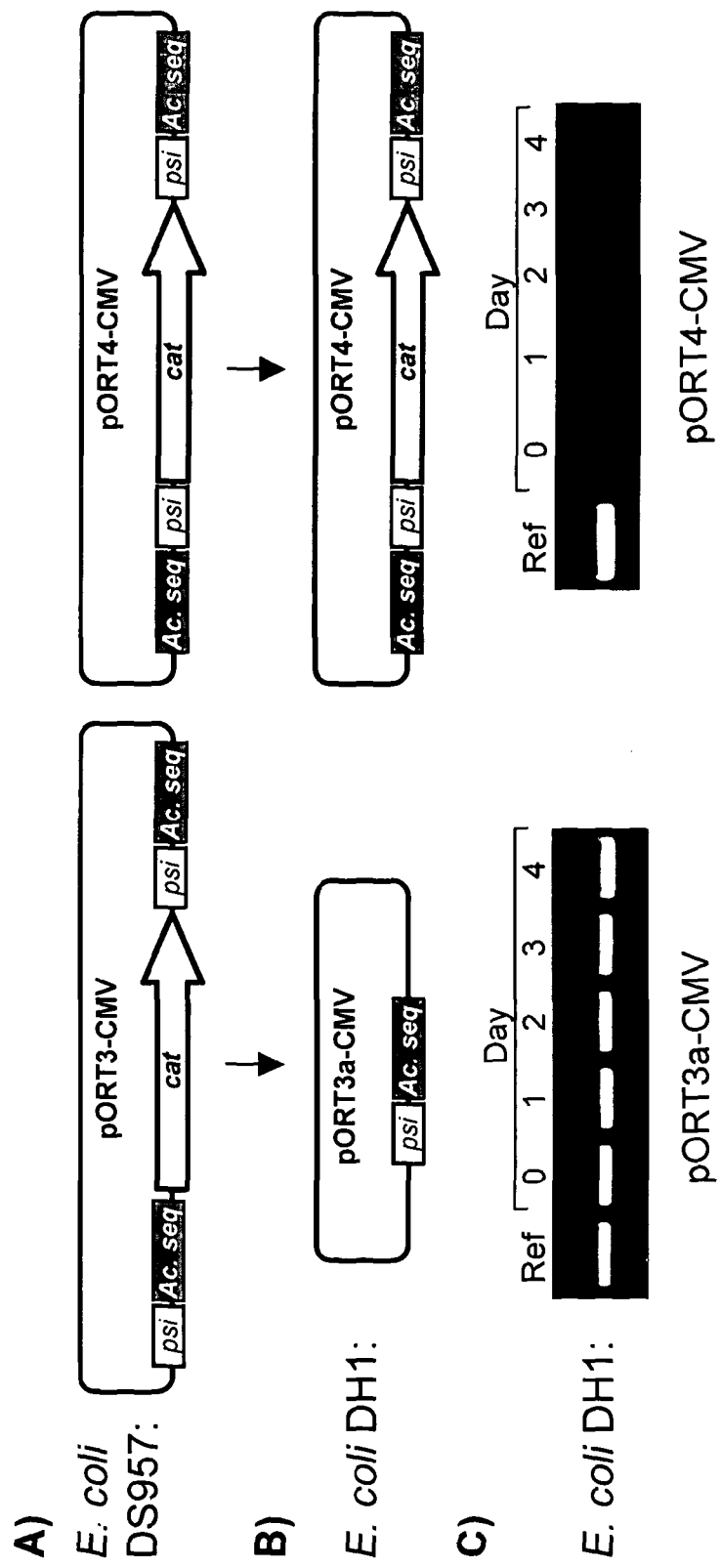
FIG. 3 A) shows the plasmids pORT3CMV and pORT4CMV as propagated in the *E. coli* pepA mutant strain DS957 ('Ac. seq.' refers to the accessory sequences containing pepA and ArgR/ArcA binding sites, 'cat' is the chloramphenicol resistance gene; other plasmid elements are not illustrated). B) shows the generation of plasmid pORT3aCMV from pORT3CMV by Xer recombination at directly repeated psi sites and accessory sequences following the transformation of the plasmids into non-mutated *E. coli* strain DH1. C) shows plasmid preparations of pORT3CMV and pORT4CMV during daily subculture in *E. coli* DH1 on an agarose gel.
Figure 4:
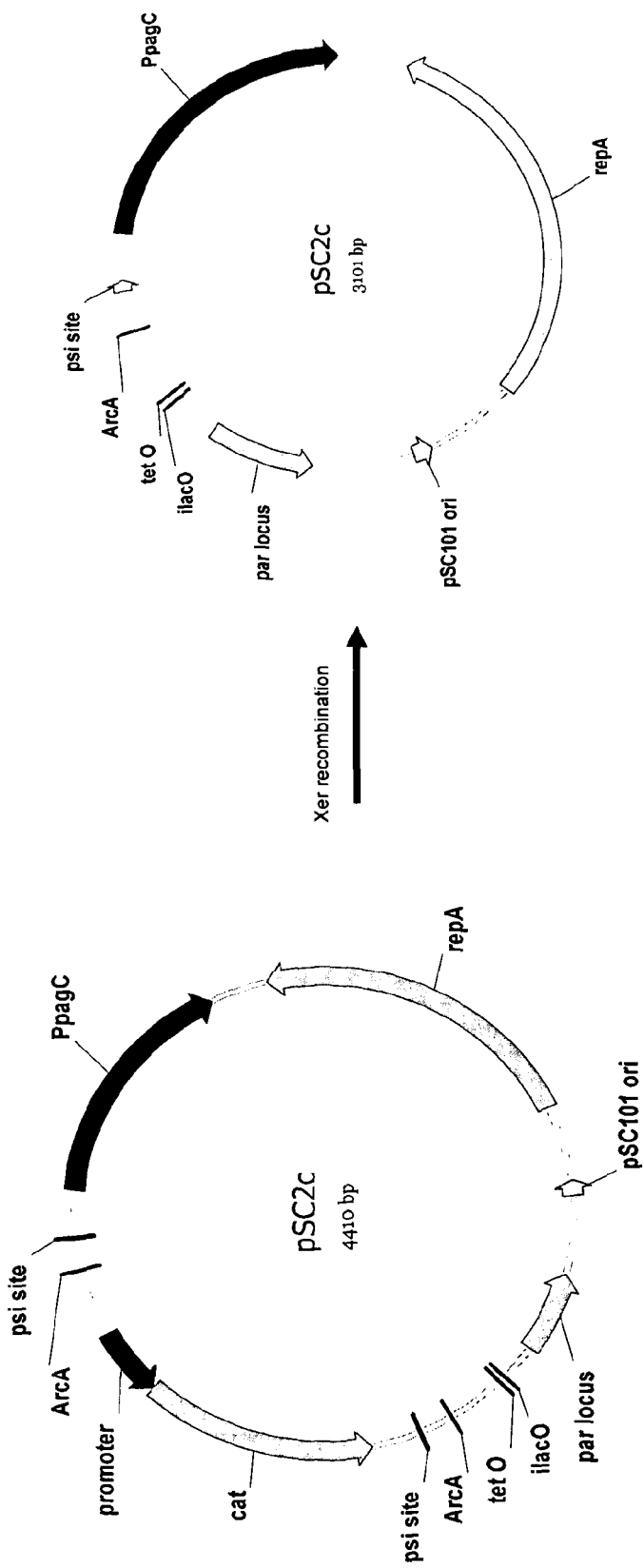
FIG. 4 shows the plasmid pSC2c and its derivative pSC2 where the cat gene has been removed following an Xer recombination event.

The eukaryotic expression plasmid pORT1-CMV was constructed from pORT1 (Cranenburgh et al. 2001. Nucleic Acids Res. 29: e26). The expression vector pcDNA3.1(+) (Invitrogen, Carlsbad, Calif.) was cut with NruI and PvuII to excise the region containing $P_{CMV}$ and bGH pA. This fragment was ligated into pORT1 that had been cut with HincII and Ecl136II to create pORT1-CMV.

The chloramphenicol resistance gene cat was amplified by PCR product from pACYC184 (New England Biolabs, Hitchin, U.K.) using primers 5'ACYC and 3'ACYC; this was then cut with AvrII, dephosphorylated using alkaline phosphatise and then cut with FseI. Two PCR products encoding the psi locus of pSC101 (DSMZ, Braunschweig, Germany) were produced with primer pairs 5AvrTPSI and 3AvrPSI and 5FsePSI and 3fSEPSI; these were cut using AvrII and FseI respectively. The pORT1-CMV plasmid was cut with AvrII and FseI and dephosphorylated.

A three-fragment ligation was used to combine the pORT1-CMV, pACYC184 and the AvrII-cut psi PCR products, generating an intermediate plasmid called pORTcatPSI. This plasmid was then cut with FseI, dephosphorylated and the FseI-cut psi PCR product ligated to create the vectors pORT3-CMV (psi sites in a direct-repeat orientation) and pORT4-CMV (psi sites in an inverted-repeated orientation).

The strains DH1(pORT3a-CMV) and DH1(pORT4-CMV) were inoculated from frozen stocks onto solid growth medium and incubated to obtain single colonies. A single colony of each strain was used to inoculate LB broth cultures. These cultures termed 'day 0' were then incubated for 24 hours. The optical density at 600 nm was measured and 'day 1' cultures inoculated at a determined optical density, the 'day 1' cultures were incubated for 24 hours. This procedure was repeated until the total number of cell generations exceeded 40. Normalised samples were taken each day and frozen for later analysis. Plasmid DNA was extracted from the frozen samples by 'mini-prep' and examined by agarose gel electrophoresis.

The site specific recombinase target sites in pORT3-CMV are in the correct relative orientation (directly repeated), such that Xer recombination in the unmodified *E. coli* DH1 cell generates the antibiotic resistance gene-free plasmid pORT3a-CMV. This plasmid is stably maintained over the period of repetitive culture (four days). The pORT4-CMV plasmid differs from pORT3-CMV only by the site specific recombinase target sites being in the incorrect relative orientation (invertedly repeated). When pORT4-CMV is transformed into the same strain of unmodified *E. coli* DH1, Xer recombination cannot take place, so the antibiotic resistance gene is retained. The metabolic burden from the antibiotic resistance gene resulted in pORT4-CMV being lost from the cells after only two days of repetitive culture. This demonstrates the retention of a selectable marker gene-free plasmid in a bacterial cell that has not been modified to contain an active plasmid maintenance system.

EXAMPLE 2

To construct the low copy number expression vector pSC2c, primers Tetlaccat1 and Tetlaccat2 were used to amplify the psi-flanked cat gene cassette of pORT3-CMV and introduce the lac operator upstream of it. This PCR product was cloned into pCR2.1, generating pCRcatpsi. The origin of replication of pSC101 was amplified by PCR using primers a101 and as101 and cloned into pCR2.1-TOPO, generating pCR101. A BspHI fragment of pCRcatpsi including the psi-flanked cat gene cassette was ligated with the BspHI fragment of pCR101 to generate p101cat. The pagC promoter was generated by PCR from *Salmonella* genomic DNA using primers Ndepag1 and Bsppag1. The PCR product was cloned into pCR2.1, generating pCRpag1. PCR primers Notpag1 and Notpag2 were used to amplify the pagC promoter from pCRpag1. The NotI-treated PCR product was cloned into NotI-cut p101cat to generate pSC2c. *E. coli* pepA mutant strains were used for cloning operations where required.

The pSC2c plasmid was transformed into *Salmonella enterica* serovar *Typhimurium* SL3261, and transformants were initially selected on LB agar plates containing chloramphenicol. Single colonies were isolated and cultured overnight in LB broth in the absence of the antibiotic. Xer recombination resulted in the deletion of the cat gene to generate pSC2, and chloramphenicol-sensitive colonies of SL3261 (pSC2) were identified.

Figure 5:
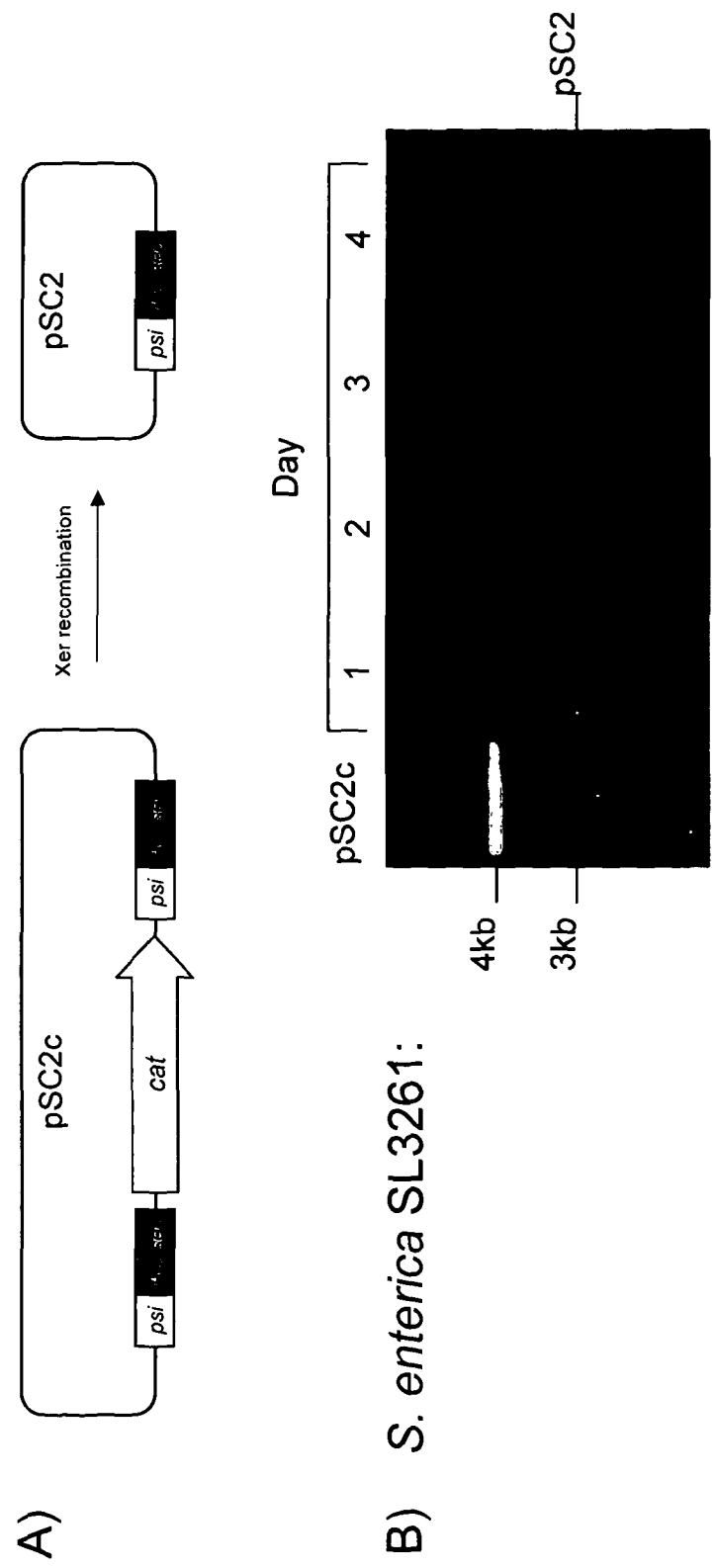
FIG. 5 A) shows the generation of plasmid pSC2 from pSC2c by Xer recombination at directly repeated psi sites and accessory sequences; B) shows an agarose gel with NdeI digestions of pSC2c from the *E. coli* pepA mutant strain DS957, and of pSC2 during a four-day subculture in *Salmonella enterica* serovar *Typhimurium* strain SL3261.

To assess plasmid maintenance, a single colony of SL3261 (pSC2) was inoculated into LB broth and incubated for 24 h ("day 1" on FIG. 5B). The optical density at 600 nm was measured and a second LB broth culture was started at a determined optical density. This procedure was repeated over 4 days until the total number of cell generations exceeded 40. Normalised cell samples were collected each day and plasmid DNA was extracted. These were linearised by NdeI digestion and subjected to agarose gel electrophoresis. Plasmid DNA prepared from *E. coli* pepA mutant strain DS957 was used as reference (pSC2c in FIG. 5B). The plasmid was stably maintained over the four days of repetitive culture, indicating that this invention is also applicable to low copy number plasmids in *Salmonella*.

REFERENCES

Barre et al. 2000 Genes Dev. 14: 2976-2988
Bentley et al. 1990, Biotechnol. Bioeng. 35: 668-681
Birnboim and Doly 1979, Nucleic Acids Res. 7: 1513-1523
Blakely et al. Cell 1993, 75: 351-361
Bloor and Cranenburgh 2006, Appl. Environ. Microbiol. 72: 2520-2525
Colloms et al. 1998 Mol. Microbiol. 28(3): 521-530
Cornet et al. 1994, J. Bacteriol. 176: 3188-3195
Cranenburgh et al. 2001. Nucleic Acids Res. 29: e26
Cranenburgh 2005, WO06/003412
Dale and Ow 1991, Proc. Natl. Acad. Sci. USA 88: 10558-10562
Datsenko and Wanner 2000, Proc. Natl. Acad. Sci. USA 97: 6640-6645
Degryse 1991, Mol. Gen. Genet. 227: 49-51
Ebinuma et al. 2001, Plant Cell Rep. 20: 383-392
Leckenby et al. 2009, Microb. Pathog. 46: 201-206
Leslie and Sherratt 1995, EMBO J. 14: 1561-1570
McNeil et al., 2000, Appl. Environ. Microbiol., 66: 1216-1219
Neilson et al. 1999, Mol. Microbiol. 31: 915-926
Neu 1992, Science 257 1064-1073
Pham et al. 2002, J. Bacteriol. 184: 1607-1616
Recchia et al. 1999, EMBO J. 18: 5724-5734
Recchia and Sherratt 1999, Mol. Microbiol. 34: 1146-1148
Sanchis et al. 1997, Appl. Environ. Microbiol. 63: 779-784
Sambrook Molecular Cloning; A Laboratory Manual, Second Edition, 1989
Sciochetti et al. 1999, J. Bacteriol. 181: 6053-6062
Sciochetti et al. 2001, J. Bacteriol. 183: 1058-1068
Sugita et al. 2000, Plant J. 22:461-469
Summers and Sherratt 1984, Cell 36: 1097-1103
Trigueros et al. 2009, Nucleic Acids Res. 37: 3580-3587
Wulff et al. 1993, Mol. Microbiol. 9: 261-271
Zubko et al. 2000, Nature Biotechnol. 18: 442-445

The invention claimed is:

1. A method of producing a selectable marker gene-free plasmid comprising the steps of:
   a) culturing a plasmid containing a selectable marker gene flanked by site specific recombinase target sites selected from Ecdif, cer, psi, pif and mwr in a first host cell environment which is incapable of effecting recombination between the site specific recombinase target sites, wherein the first host cell environment comprises an inactivating mutation in one or more of the genes encoding PepA, ArgR and ArcA; and
   b) subsequently culturing the plasmid in a second host cell environment which is capable of effecting recombination between the site specific recombinase target sites, such that the selectable marker gene is excised, wherein the second host cell environment contains active versions of PepA and ArgR or ArcA, and comprises a site specific recombinase selected from XerC and XerD.

2. The method of claim 1 further comprising the step of:
   c) maintaining the selectable marker gene-free plasmid in cell culture.

3. The method of claim 1 further comprising the step of:
   d) isolating the selectable marker gene-free plasmid from the second host cell environment.

4. The method of claim 1 wherein the first host cell environment and the second host cell environment are within different cells.

5. The method of claim 1, wherein the first host cell environment and the second host cell environment are formed within the same host cell.

6. The method of claim 5 wherein the first host cell environment and the second host cell environment are temporally separated.

7. The method of claim 1 wherein the selectable marker gene is an antibiotic resistance gene.

8. The method of claim 1 wherein the selectable marker gene enables the production of a metabolite essential for but absent from the first and/or the second host cell environment.

9. The method according to claim 1 wherein the first host cell environment and/or the second host cell environment is a Gram-negative bacterial cell.

10. The method according to claim 9 wherein the first host cell environment and the second host cell environment are independently selected from the genera *Escherichia, Salmonella, Shigella, Agrobacterium, Pseudomonas* and *Vibrio*.

11. The method of claim 1 wherein the plasmid encodes one or more genes of interest.

\* \* \* \* \*

SEQUENCE LISTING

```
<160> NUMBER OF SEQ ID NOS: 30

<210> SEQ ID NO 1
<211> LENGTH: 28
<212> TYPE: DNA
<213> ORGANISM: Escherichia coli

<400> SEQUENCE: 1
ggtgcgcata atgtatatta tgttaaat                                            28

<210> SEQ ID NO 2
<211> LENGTH: 30
<212> TYPE: DNA
<213> ORGANISM: Escherichia coli

<400> SEQUENCE: 2
ggtgcgtaca attaagggat tatggtaaat                                          30

<210> SEQ ID NO 3
<211> LENGTH: 27
<212> TYPE: DNA
<213> ORGANISM: Salmonella enterica

<400> SEQUENCE: 3
gtgcgcgcaa gatccattat gttaaac                                             27

<210> SEQ ID NO 4
<211> LENGTH: 28
<212> TYPE: DNA
<213> ORGANISM: Artificial Sequence
<220> FEATURE:
<223> OTHER INFORMATION: dif-psi hybrid

<400> SEQUENCE: 4
ggtgcgcgca agatccatta tgttaaat                                            28

<210> SEQ ID NO 5
<211> LENGTH: 28
<212> TYPE: DNA
<213> ORGANISM: Klebsiella pneumoniae

<400> SEQUENCE: 5
```

```
ggtgcacgca acagatgtta tggtaaat                               28

<210> SEQ ID NO 6
<211> LENGTH: 28
<212> TYPE: DNA
<213> ORGANISM: Bacillus subtilis

<400> SEQUENCE: 6
acttcctaga atatatatta tgtaaact                               28

<210> SEQ ID NO 7
<211> LENGTH: 34
<212> TYPE: DNA
<213> ORGANISM: Bacteriophage P1

<400> SEQUENCE: 7
ataacttcgt ataatgtatg ctatacgaag ttat                        34

<210> SEQ ID NO 8
<211> LENGTH: 33
<212> TYPE: DNA
<213> ORGANISM: Saccharomyces cerevisiae

<400> SEQUENCE: 8
gaagttccta ttctctagaa agtataggaa ctt                         33

<210> SEQ ID NO 9
<211> LENGTH: 31
<212> TYPE: DNA
<213> ORGANISM: Saccharomyces cerevisiae

<400> SEQUENCE: 9
ttgatgaaag aatacgttat tctttcatca a                           31

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
attacctagg atccgcttat tatcacttat tcagg                       35

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
attaggccgg ccaaatcagt aagttggcag cat                         33

<210> SEQ ID NO 12
<211> LENGTH: 55
<212> TYPE: DNA
<213> ORGANISM: Artificial Sequence
<220> FEATURE:
<223> OTHER INFORMATION: Primer

<400> SEQUENCE: 12
attacctagg tcatgaagct tatcatcgat aagctcatag acagcctgaa acagg  55
```

```
<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
attacctagg atggtgttaa gcgggcgg                                      28

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
attaggccgg cccatagaca gcctgaaaca gg                                 32

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
attaggccgg cctcatgaat ggtgttaagc gggcgg                             36

<210> SEQ ID NO 16
<211> LENGTH: 215
<212> TYPE: DNA
<213> ORGANISM: Salmonella enterica

<400> SEQUENCE: 16
gcctcccgtg gggaaaaaat catggcaatt ctggaagaaa tagcgctttc agccggcaaa   60
cctgaagccg gatctgcgat tctgataaca aactagcaac accagaacag cccgtttgcg  120
ggcagcaaaa cccgtacttt tggacgttcc ggcggttttt tgtggcgagt ggtgttcggg  180
cggtgcgcgc aagatccatt atgttaaacg ggcga                             215

<210> SEQ ID NO 17
<211> LENGTH: 27
<212> TYPE: DNA
<213> ORGANISM: Salmonella enterica

<400> SEQUENCE: 17
ggtgcgcgca agatccatta tgttaaa                                       27

<210> SEQ ID NO 18
<211> LENGTH: 10
<212> TYPE: DNA
<213> ORGANISM: Salmonella enterica

<400> SEQUENCE: 18
ataacaaact                                                          10

<210> SEQ ID NO 19
<211> LENGTH: 215
<212> TYPE: DNA
<213> ORGANISM: Escherichia coli

<400> SEQUENCE: 19
```

```
gtgaaaccat gaaaatggc agcttcagtg gattaagtgg gggtaatgtg gcctgtaccc    60
tctggttgca taggtattca tacggttaaa atttatcagg cgcgatcgcg cagttttag    120 ggtggtttgt tgccattttt acctgtctgc tgccgtgatc gcgctgaacg cgttttagcg   180
gtgcgtacaa ttaagggatt atggtaaatc cactt                             215
```

<210> SEQ ID NO 20
<211> LENGTH: 30
<212> TYPE: DNA
<213> ORGANISM: Escherichia coli

<400> SEQUENCE: 20

```
ggtgcgtaca attaagggat tatggtaaat                                    30
```

<210> SEQ ID NO 21
<211> LENGTH: 18
<212> TYPE: DNA
<213> ORGANISM: Escherichia coli

<400> SEQUENCE: 21

```
gttgcatagg tattcata                                                 18
```

<210> SEQ ID NO 22
<211> LENGTH: 216
<212> TYPE: DNA
<213> ORGANISM: Klebsiella pneumoniae

<400> SEQUENCE: 22

```
aagaagaaca tcggaaacag gacttactcc ggctgaatgg tgtgaaattc tgcgctatgc    60
acttgcgcgc atactcatgc atgccgtaaa aacagagcct gcgcgtttct ggcgggtttt   120
cgggtggttt gttgcctgtt ttaccggttt cccgtcagaa acgccctgag ggcctctcag   180
gcggtgcacg caacagatgt tatggtaaat acaatg                             216
```

<210> SEQ ID NO 23
<211> LENGTH: 28
<212> TYPE: DNA
<213> ORGANISM: Klebsiella pneumoniae

<400> SEQUENCE: 23

```
ggtgcacgca acagatgtta tggtaaat                                      28
```

<210> SEQ ID NO 24
<211> LENGTH: 18
<212> TYPE: DNA
<213> ORGANISM: Klebsiella pneumoniae

<400> SEQUENCE: 24

```
cgcgcatact catgcatg                                                 18
```

<210> SEQ ID NO 25
<211> LENGTH: 45
<212> TYPE: DNA
<213> ORGANISM: Artificial Sequence
<220> FEATURE:
<223> OTHER INFORMATION: Primer

<400> SEQUENCE: 25

```
attatcatga aattgtgagc gctcacaatt agcttatcat cgata                   45
```

<210> SEQ ID NO 26
<211> LENGTH: 22

```
<212> TYPE: DNA
<213> ORGANISM: Artificial Sequence
<220> FEATURE:
<223> OTHER INFORMATION: Primer

<400> SEQUENCE: 26
attatcatga atggtgttaa gc                                              22

<210> SEQ ID NO 27
<211> LENGTH: 69
<212> TYPE: DNA
<213> ORGANISM: Artificial Sequence
<220> FEATURE:
<223> OTHER INFORMATION: Primer

<400> SEQUENCE: 27
tggtcgaccc gggatcctct agaggcctaa taacatatga caactcctta atactactta    60
ttatttacg                                                            69

<210> SEQ ID NO 28
<211> LENGTH: 46
<212> TYPE: DNA
<213> ORGANISM: Artificial Sequence
<220> FEATURE:
<223> OTHER INFORMATION: Primer

<400> SEQUENCE: 28
catgattttt tattcaacga agagttaacc actcttaata ataatg                   46

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
gatccactag tagcggccgc c                                              21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tagatgcatg ctcgagcggc                                                20
```